(12) United States Patent
Gainey (10) Patent No.: US 8,834,396 B2
(45) Date of Patent: Sep. 16, 2014

(54) BUILD-A-BOOT

(76) Inventor: Jeffrey W. Gainey, Peachtree City, GA (US)

( * ) Notice: Subject to any disclaimer, the term of this patent is extended or adjusted under 35 U.S.C. 154(b) by 480 days.

(21) Appl. No.: 13/065,955

(22) Filed: Apr. 2, 2011

(65) Prior Publication Data

US 2011/0180074 A1    Jul. 28, 2011

Related U.S. Application Data

(63) Continuation-in-part of application No. 12/287,136, filed on Oct. 7, 2008, now abandoned.

(51) Int. Cl.
| | |
|---|---|
| A61F 5/00 | (2006.01) |
| A61F 5/37 | (2006.01) |
| A47C 20/02 | (2006.01) |
| A61F 13/06 | (2006.01) |
| A61F 5/01 | (2006.01) |
| A61F 5/058 | (2006.01) |

(52) U.S. Cl.
CPC ............. *A61F 5/0195* (2013.01); *A61F 13/069* (2013.01); *A61F 5/0585* (2013.01)
USPC ................................ 602/23; 128/882; 5/649

(58) Field of Classification Search
USPC .......... 128/882, 869, 846; 602/23, 24, 25, 26, 602/27, 28, 29, 65, 62, 66; 5/648–651
See application file for complete search history.

(56) References Cited

U.S. PATENT DOCUMENTS

| | | | |
|---|---|---|---|
| 4,076,022 A | 2/1978 | Walker | |
| 4,186,738 A * | 2/1980 | Schleicher et al. | 128/892 |
| 5,328,445 A | 7/1994 | Spahn et al. | |
| 5,367,789 A | 11/1994 | Lamount | |
| 5,449,339 A * | 9/1995 | Drennan | 602/23 |
| 5,569,174 A * | 10/1996 | Varn | 602/27 |
| D411,758 S | 7/1999 | Karim | |
| 6,256,804 B1 | 7/2001 | Stevens | |
| 6,640,810 B1 * | 11/2003 | Callsen et al. | 128/882 |
| 2009/0084390 A1 * | 4/2009 | Davis et al. | 128/882 |

* cited by examiner

*Primary Examiner* — Patricia Bianco
*Assistant Examiner* — Tarla Patel
(74) *Attorney, Agent, or Firm* — J.T. Hollin, Jr., Attorn at Law, P.C.

(57) ABSTRACT

A heel supporting and protective boot for bed-ridden patients, comprising unitary exterior and interior body forms which contain fiber filling and an angled foam wedge. Sewn tube holes on both sides allow for insertion of medical tubing. The inner fabric of the boot is antibacterial and moisture absorbent, while the outer fabric is moisture repellant. Left and right "Y-straps" provide secure upper and lower fastening of the boot as it envelops the patient's foot and lower leg. Two "loop" straps and a T-stabilizer stabilize the boot and keep the foot at a 90 degree angle to help eliminate foot drop. An opening at the heel of the boot and a circular cutout in the foam wedge allow the heel to remain exposed to air, provide proper elevation, and enhance blood circulation. The device enhances the healing of existing ulcers and minimizes the occurrence of foot drop and new pressure points.

6 Claims, 8 Drawing Sheets

BUILD-A-BOOT

REFERENCES TO RELATED APPLICATIONS

This application is a continuation-in-part of U.S. patent application Ser. No. 12/287,136 filed on Oct. 7, 2008, and which is incorporated fully herein by reference.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

REFERENCE TO A "SEQUENCE LISTING," A TABLE, OR A COMPUTER PROGRAM LISTING APPENDIX

Not applicable.

BACKGROUND OF THE INVENTION (1) Field of the Invention

This invention relates to the prevention or cure of heel sores for bed patients. The product is a medical boot that utilizes a unique combination of angled foam and fiber. The boot includes several other features that enhance the healing and prevention of heel sores while ensuring no other medical problems are created for the patient.

Heretofore several different foot and leg devices have been proposed for the cure or prevention of heel sores. These sores are known more specifically as decubitus ulcers, and generally form by frictional irritation between the heel of a bed ridden patient and the bed linens or mattress. Lying in a particular position for a prolonged period produces external pressures on skin and tissues covering rigid or bony body parts, such as the heel. This pressure compromises the blood supply to those rigid or bony areas which, after a sustained period, results in "bed sores."

(2) Description of the Related Art

The following is a listing of patents issued for products intended to relieve heel pressure and thus resolve the problem of bed sores. Next to each listing is a brief description of the mechanics or method of their product.

U.S. Pat. No. 4,076,022 Therapeutic foot and leg protector—contains a rigid outer shell having a soft, protective liner. The protector is perforated in the heel portion for air circulation.

U.S. Pat. No. 6,256,804 Body Supports and protectors— The pillows and supports are made for supporting various body parts, namely neck, shoulder, torso, elbows, tail bone.

U.S. Pat. No. 5,328,445 Inflatable foot cushion—uses several, movable inflatable foot cushions and also involves the use of a shoe spoon and rigid base.

U.S. Pat. No. D411,758 Ornamental design for a heel protector. Product utilizes foam.

U.S. Pat. No. 5,367,789 is a protective medical boot and orthotic splint—a soft medical boot with splint bar for adjusting angle of the foot. The device comprises a rigid insole, rigid splint bar, hinge internal sac filled with air/water/gel, and a rubberized laminated sole.

U.S. Pat. No. 5,449,339 Heel supporting protective boot for bed patients—foam with foot and leg supporting portions. The invention features friction reducing material and extra padding composed of foam, serving to limit foot drop.

Although a number of devices have been developed for supporting and protecting the heels of bed patients, these devices have been subject to a number of difficulties and disadvantages which include the tendency to come loose, or become disengaged from the patient as a result of patient movement and activity. Some products that use foam cushioning only, can create additional pressure points on the patient's leg. Products that use fiber filling only can provide some cushioning but cannot sufficiently elevate the heel. These products do not off-load pressure from the heel, they only reduce heel pressure. Further, these prior art devices also have not heretofore allowed for the use of medical tubing, such as sequential compression pumps, to be used simultaneously with the patient's treatment.

The vast majority of prior art devices does not effectively relieve and reduce pressure and friction between the heel or joint of the patient and the bedding surface. Further, the structure of these devices allows a patient's foot to drop below a 90 degree angle, causing foot contracture and decreasing blood flow. Most of these devices can become soiled due to patient incontinency. Unfortunately, many devices are hot and uncomfortable to wear and cause a buildup of high temperatures. These conditions enhance the formation of decubitus ulcers. Many prior art products actually create high pressure contact points against the patient's body and therefore often cause sores to develop. In addition, these devices allow for internal/external rotation of the leg causing other joint and hip problems. Many of these devices are designed from untreated foam alone and such material can actually harbor bacteria.

OBJECTS AND SUMMARY OF THE INVENTION

It is an object of the present invention to provide a new and improved heel boot for bed patients which eliminates many of the disadvantages and problems encountered with prior art devices.

It is another object of the present invention to provide a new and improved heel supporting boot of the character described which is especially useful in the prevention or cure of bed sores on the heel.

Another object of the present invention is to provide a new and improved heel supporting boot which eliminates friction and pressure contact between the patient's heel and the bedding surface.

Another object of the invention is to provide an improved method of elevating the heel without hyper-extending the knee. Adequate elevation also facilitates the exposure of the heel to the circulation of air.

Another object of the invention is to provide sewn holes in each side of the medical boot so that a sequential compression pump or other necessary medical tubing can be used with the product.

Another object of the invention is to utilize the cushioning effect of a combination of fiber fill and an angled foam wedge, such the goal of healing/preventing decubitis ulcers are met.

Another object of the invention is to provide a new medical boot that does not allow bacteria to grow inside the boot.

Another object of the invention is to provide a new product that utilizes moisture absorbing fabric on the interior, and additionally, is fabricated with a moisture repelling fabric on the exterior.

Another object of the invention is to provide a new method of secure and effective strapping with the purpose of preventing foot drop of bed ridden patients.

Another object of the invention is to utilize a material that will ensure necessary air ventilation and minimize internal heat buildup.

Another object of the invention is to utilize a horizontally flat design shape of the foam wedge, coupled with a T-bar stabilizer, to effectively inhibit internal or external rotation of the patient's leg, thus avoiding knee and hip joint problems.

Another object of this invention is to ensure ease of operation of the device for the caregiver, with respect to putting on and taking off the device. At the same time, the device disclosed is designed so as to practically eliminate inadvertent disengagement of the patient's foot.

A further object of the invention is to provide a better product that will not soil due to patient incontinence.

Another object of the invention is to ensure that are no pressure points are created within the boot while maintaining adequate elevation of the patient's heel.

Another object of the invention is to provide effective healing care for patients regardless of their size or weight.

Another object of the invention is to provide a product which is economical to manufacture and simple to utilize by nursing personnel while accomplishing a multitude of healing goals.

BRIEF DESCRIPTION OF THE INVENTIVE CONCEPT

The foregoing objects and advantages of the present invention are accomplished in an illustrated embodiment disclosed herein, which embodiment comprises a new and improved heel-supporting protective boot for bed-ridden patients. The boot has a unique combination of foam and fiber materials fabricated within the base, or bottom of the boot. The foam is in the form of a foam wedge that may be constructed of either one or two pieces that are used singly or combined to provide a flat, wide base and an angled or sloped upper piece. The fiber consists of any of several materials that provide a soft, pliable, medium-dense texture. The flat, wide base is utilized to discourage internal/external rotation of the patient's leg. The angled or sloped top or upper piece is utilized to ensure the patient's heel remains comfortably elevated and exposed to air without hyper-extending the knee joint. By elevating the heel, combined with a circular cutout, which allows suspension of the heel itself, pressure is offloaded, not just reduced.

The combination of fiber fill and the foam wedge work together to eliminate or significantly reduce any pressure points created by the use of a foam component alone. The foam/fiber combination extends under the ankle and terminates at a point above the patient's heel so the device is out of contact with the heel. The boot includes a left sidewall and a right sidewall designed to support the patient's lower leg and foot. The leg support fiber/foam portion extends between the sidewalls to support the patient's leg with the heel elevated well above and out of contact with the bedding. The heel is completely elevated and thus exposed to air circulation by means of the circular cutout.

The medical boot also has tube holes sewn in each sidewall that allow for the use of medical tubing in conjunction with the use of the boot. The type of medical tubing typically utilized would be a sequential compression pump.

The boot additionally uses dual types of fabric for its exterior and interior covering. An outer fabric repels any fluid that may come into contact with the boot. An inner fabric, which may comprise a brushed micro-suede material, absorbs fluids, like perspiration, and also is antibacterial.

The boot is fabricated with left and right "Y-straps" that provide secure upper and lower fastening of the boot as it envelops the patient's foot and lower leg. Finally, the boot also uses two "loop" straps which keep the foot at a 90 degree angle and help eliminate foot drop. By eliminating foot drop, essential blood flow is enhanced and heel cord tightening is eliminated. A 90 degree angle, as measured between the plane of the sole of a patient's foot and his/her shinbone, is the optimum foot orientation which allows adequate blood circulation.

BRIEF DESCRIPTION OF THE DRAWINGS

For a better understanding of the invention, reference should be had to the following descriptions taken in conjunction with the drawings.

| Table of Nomenclature & Part Numbers of Invention | |
|---|---|
| 1. | Foam wedge |
| 2. | Foam wedge slope |
| 2(a). | Leg rest |
| 2(b). | Achilles tendon rest |
| 3. | Foam wedge bottom |
| 4. | Circular cutout |
| 5. | Inner base |
| 6. | Left foot portion |
| 7. | Right foot portion |
| 8. | Fiber |
| 9. | Left sidewall |
| 10. | Right sidewall |
| 11. | Horizontal hook strap |
| 12. | Right upper Y-strap |
| 13. | Right lower Y-strap |
| 14. | Right Y-strap loop fastener |
| 15. | Left upper Y-strap |
| 16. | Left lower Y-strap |
| 17. | Left Y-strap loop fastener |
| 18. | Stitching |
| 19. | Lower loop strap |
| 20. | Upper loop strap |
| 21. | Left sewn hook piece |
| 22. | Right sewn hook piece |
| 23. | Right inner end |
| 24. | Left inner end |
| 25. | Outer fabric |
| 26. | Inner fabric |

-continued

Table of Nomenclature & Part Numbers of Invention

| | |
|---|---|
| 27. | Left tube hole |
| 28. | Right tube hole |
| 29. | Boot heel opening |
| 30. | Boot front seam |
| 31. | Patient's leg |
| 32. | Patient's foot |
| 33. | Boot outer bottom |
| 34. | T-stabilizer |
| 35. | T-stabilizer hook section |
| 36. | Stabilizer pocket |
| 37. | Pocket loop section |
| 38. | T-stabilizer stem |
| 39. | "Toes" tag |
| 40. | Left slot |
| 41. | Right slot |
| 42. | Left bottom strap |
| 43. | Right bottom strap |
| 44. | Items 44-49 n/a |
| 50. | Front edge of foam wedge |
| 51. | Rear edge |
| 52. | Length of foam wedge |
| 53. | Ridge |
| 54. | Toe area fiber fill |
| 55. | Achilles tendon area fiber fill |
| 56. | Calf area fiber fill |

DESCRIPTION OF THE PREFERRED EMBODIMENT

Referring now more particularly to the drawings herein, there is illustrated a new and improved heel supporting medical boot that utilizes several features combined to create a new and unique product.

Figure 1:
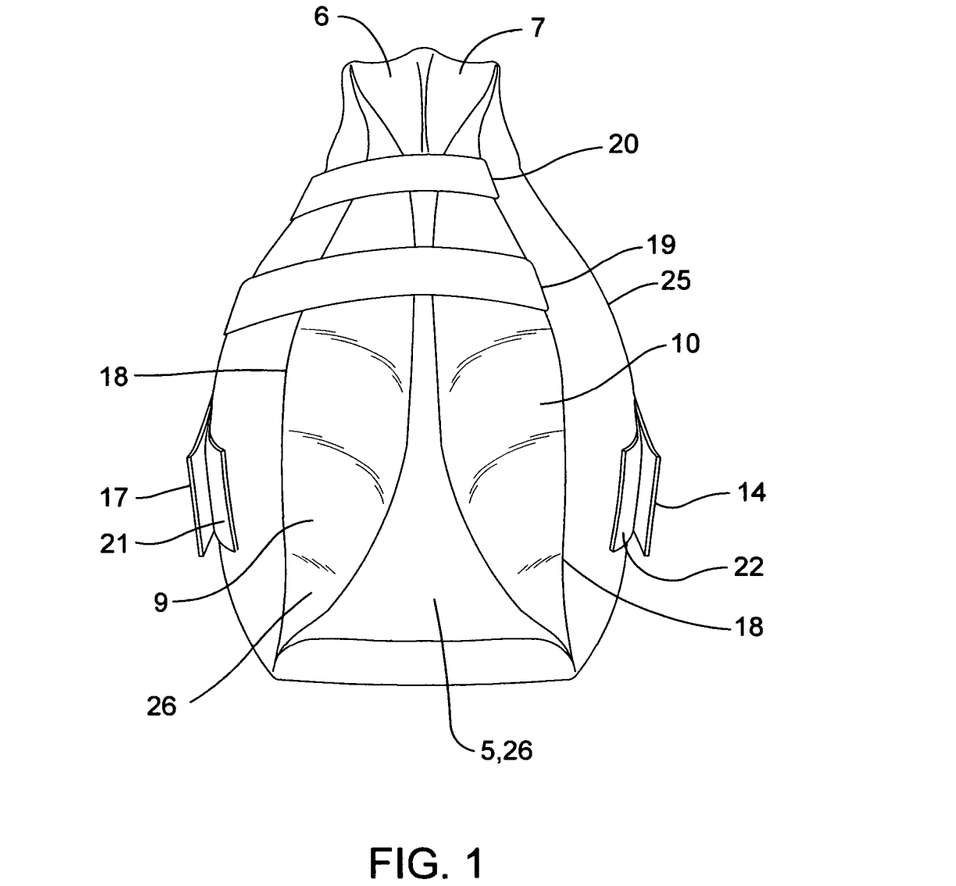
FIG. 1 is a view of the medical boot from the rear opening framed by the left and right sidewalls, between which a patient's foot is inserted.

FIG. 1 is a view of the rear of the medical boot, which is the end wherein a patient's foot is initially inserted. Prominent components shown are the left sidewall 9, the right sidewall 10, the inner base 5 of the boot, and the lower and upper loop straps 19, 20. The lower and upper loop straps 19, 20, must be unfastened in order to separate the left and right sidewalls, 9, 10 and allow insertion of the patient's foot. The inner base 5, and the left and right sidewalls 9, 10 are filled with a pliable fibrous material, as is the inner base 5 of the boot. The outer fabric 26 covering the exterior surfaces of the left and right sidewalls 9, 10, is a "rip stop" type fabric, a woven, nylon-threaded material which is generally water resistant. The inner fabric 25, covering the interior surfaces of the sidewalls 9, 10 and the inner base 5 of the boot, may comprise a brushed, micro-suede material, or similar material, that is treated to exhibit anti-bacterial qualities. The inner fabric 25 and the outer fabric 26 are separated by a continuous junction, as shown by stitching 18.

Figure 2:
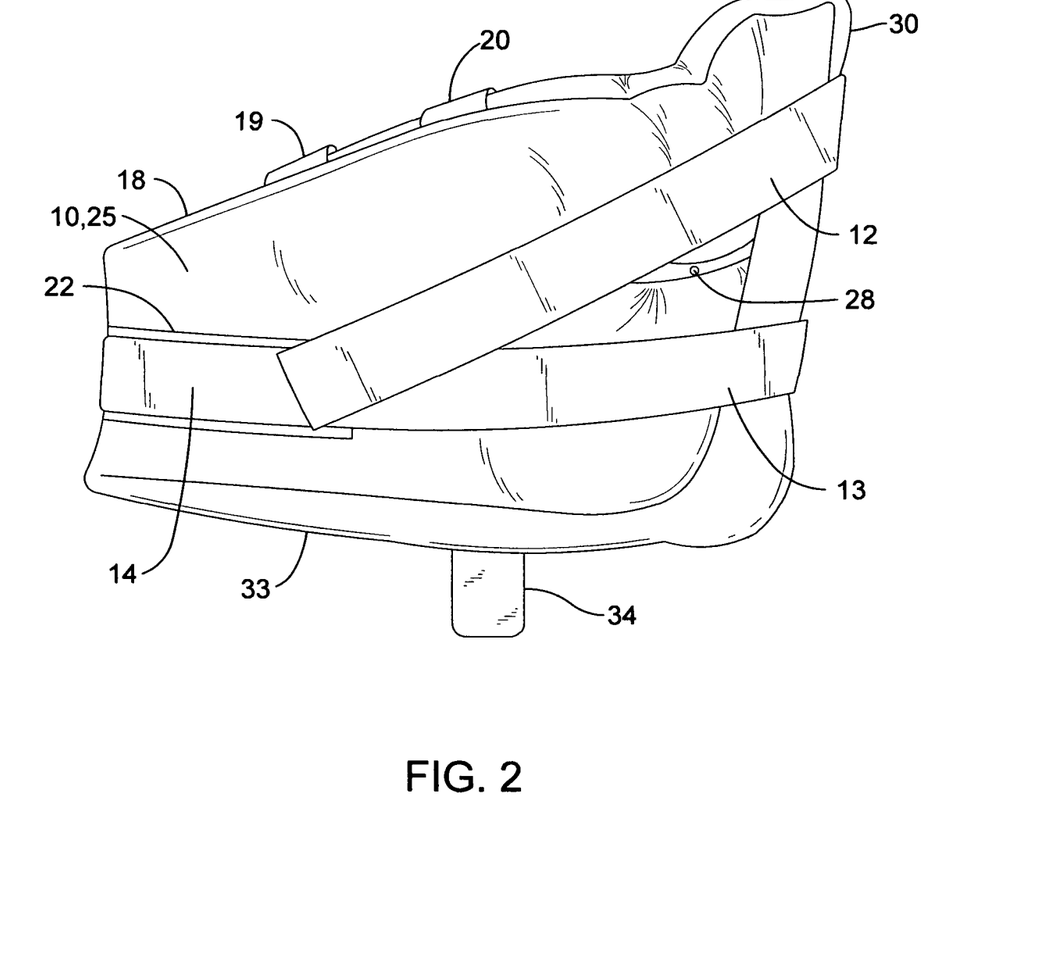
FIG. 2 is a view of the right side of the medical boot, showing the right upper and lower Y-strap.

FIG. 2 is a right side view of the medical boot, prominently showing the right upper Y-strap 12, the right lower Y-strap 13, and the right Y-strap loop fastener 14. A right sewn hook piece 22 comprises the hook component of a hook and loop type fastener, attached to the outer surface of the right sidewall 10 and serves to provide a fastening anchor for the Y-strap loop fastener 14. Also depicted is the right tube hole 28 which serves to admit the insertion of a tube that may be used with a sequential compression pump. The device T-stabilizer 34, which serves to maintain an upright orientation of the medical boot, is partly visible also. A "TOES" tag 39 is stitched to the boot front seam 30, to provide visible directions to a caregiver who must make the determination as to which end of the device the patient's foot must first be inserted.

Figure 3:
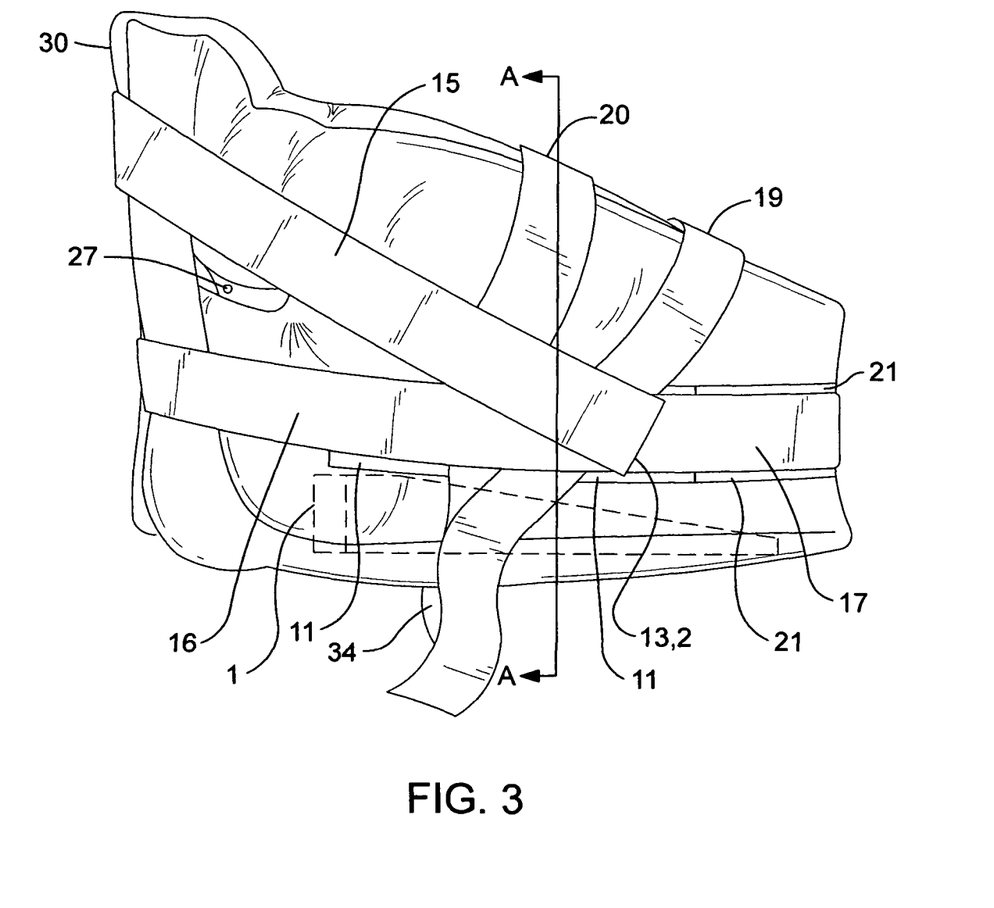
FIG. 3 is a left side view of the boot, showing the left Y-straps, along with the upper and lower loop straps.

FIG. 3 is a left side view of the medical boot, prominently showing the left upper Y-strap 15, the left lower Y-strap 16, and the left Y-strap loop fastener 17. A left sewn hook piece 21 comprises the hook component of a hook and loop type fastener, attached to the outer surface of the left sidewall 9 and serves to provide a fastening anchor for the Y-strap loop fastener 17. Also depicted in FIG. 3 is the right tube hole 27 which serves to admit the insertion of a tube that may be used with a sequential compression pump, or similar medical apparatus. The upper loop strap 20 and the lower loop strap 19 are shown as they extend from their attachment at the right sidewall 9 and are placed into secure attachment with the horizontal hook strap 11. The horizontal hook strap 11 comprises the hook component of a hook and loop-type fastener, with upper loop strap 20 and the lower loop strap 19 comprising the loop components. The medical boot's T-stabilizer 34 is partly visible, along with a hidden view of the orientation of the foam wedge 1.

Figure 4:
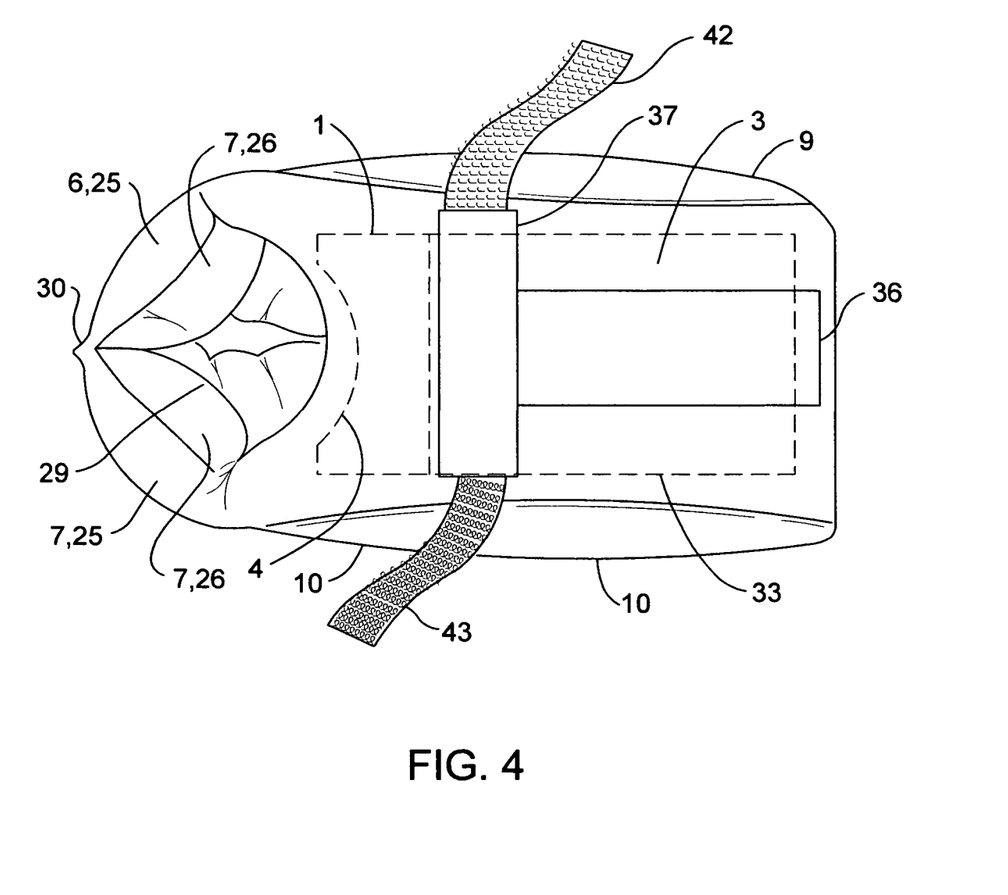
FIG. 4 shows the bottom of the boot, displaying the heel opening and the stabilizer pocket.
Figure 5:
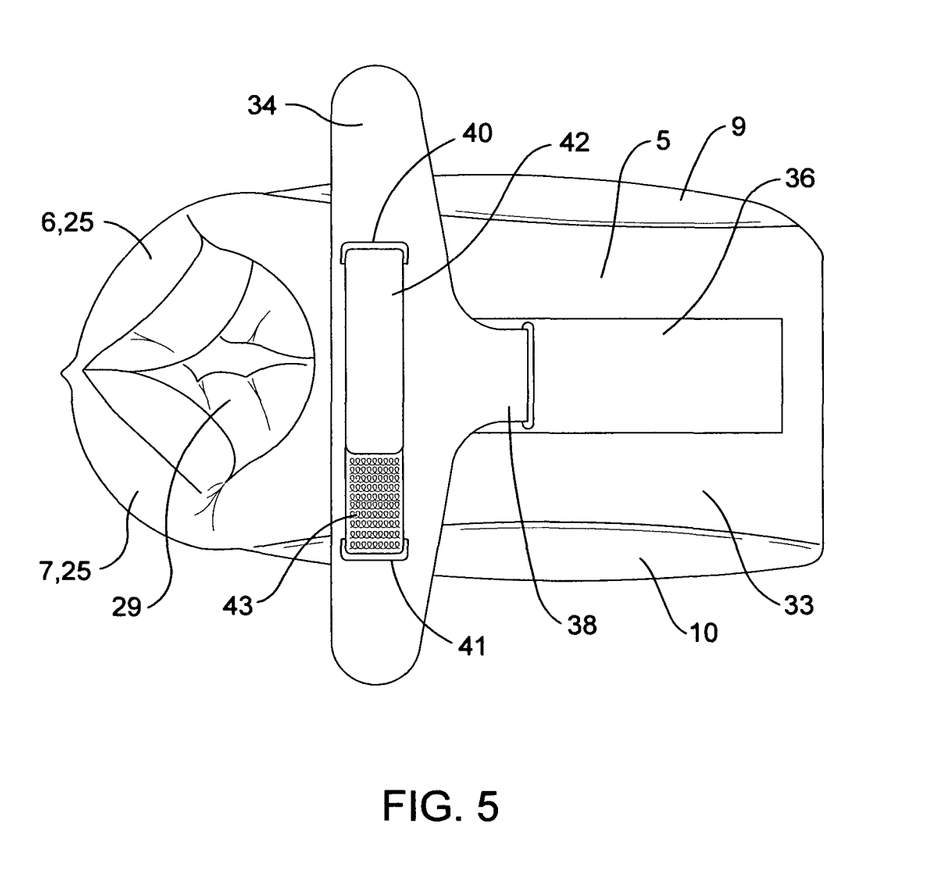
FIG. 5 illustrates the bottom of the medical boot, including the T-stabilizer inserted into the stabilizer pocket.

Moving to FIG. 4, there is shown a bottom view of the medical boot. Components of the medical boot shown include the stabilizer pocket 36 and the pocket loop section 37. The stabilizer pocket 36 receives the T-stabilizer stem 38 (shown in FIG. 6). The pocket loop section 37 is fabricated with the loop component of a hook-and-loop type fastener while the upper portion of the T-stabilizer 34 comprises the hook section 35 of a hook-and-loop type fastener. Upon assembly, the T-stabilizer hook section 35 and the pocket loop section 37 are engaged to form a secure connection and provide stable vertical orientation for the medical boot. Also shown in FIG. 4 are the boot outer bottom 33, the boot heel opening 29, and the boot front seam 30. An outline of the foam wedge 1, including its circular cutout 4 and the bottom 3 are depicted. The left foot portion of the boot 6 and the right foot portion of the boot 7 are shown. In viewing FIG. 5, it is seen that the T-stabilizer stem 38 has been inserted into the stabilizer pocket 36, with the effect of providing an additional factor of horizontal stabilization for the boot outer bottom 33.

Figure 6:
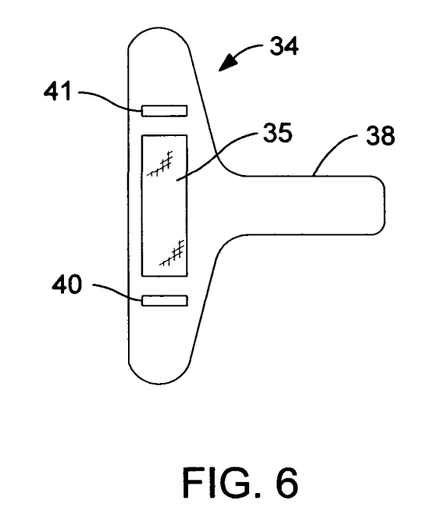
FIG. 6 shows the T-stabilizer.

FIG. 6 is a view of the T-stabilizer 34, further showing the T-stabilizer hook section 35 and the T-stabilizer stem 38. Viewing FIG. 7, there is shown a perspective view of the foam wedge 1 of the inventive concept. This wedge of foam material is used to form the base of the boot. The foam wedge 1 is wide enough at its front edge 50 to extend to the right and left side of each patient's lower leg 31, as depicted in the outline. The base 5 of the boot is of a width that ensures internal and external rotation of the leg 31 is limited. The length 52 of the foam wedge 1 extends from the patient's mid calf to their lower calf just above the ankle at the rear edge 51 of the foam wedge 1. At the rear edge 51 of the foam wedge 1, near a patient's ankle, the foam wedge has a circular cutout 4 that ensures the heel of a patient's foot 32 will remain offloaded, elevated and exposed to air.

Figure 7:
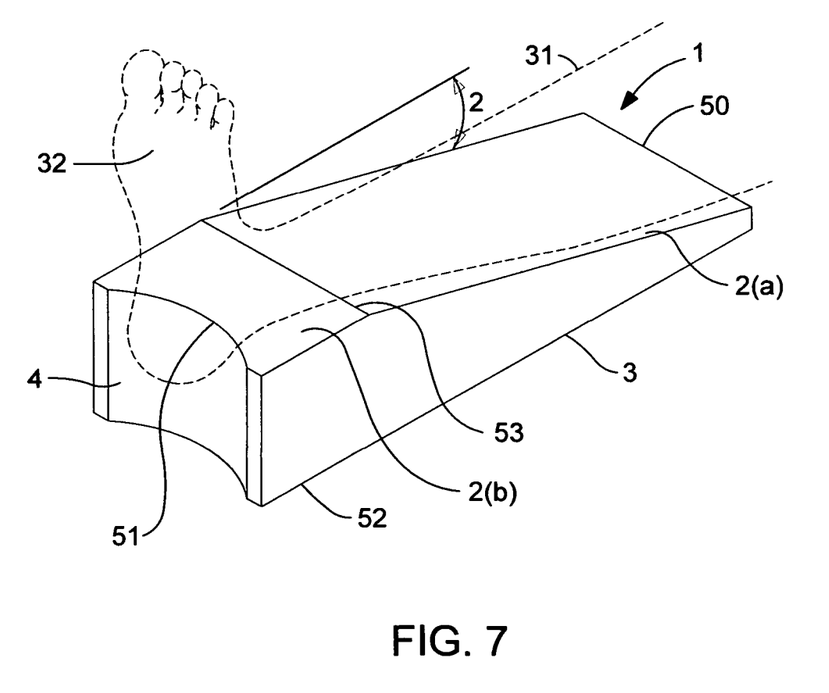
FIG. 7 depicts the outline of a patient's leg as it would be superimposed upon the foam wedge of the device.

The elevation of a patient's foot 32 and clearance of the heel helps prevent bed sores and restricted blood circulation in the foot. The medical boot is constructed of sufficient width 52, as depicted at its rear edge 50, so as to enhance horizontal stability of the boot. The foam wedge is constructed with a slope 2 upward from the rear edge 50 of the foam wedge 1 to its ridge 53 at approximately a thirty degree angle. At the ridge 53, the slope 2 ends and the remaining portion of the top of the foam wedge 1 is flat, or horizontally level in relationship to the bed surface.

Figure 8:
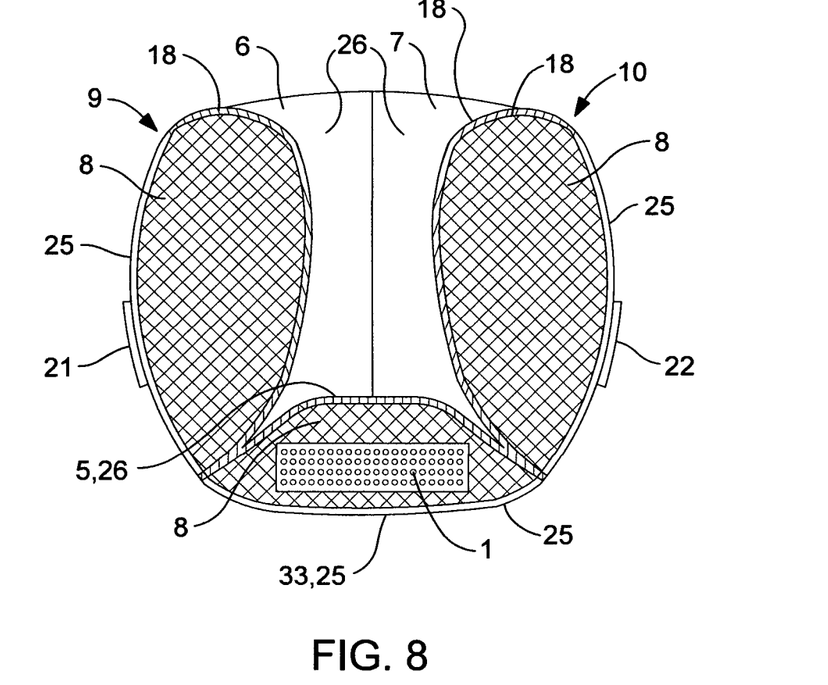
FIG. 8 is a cutaway view of the medical boot depicting the orientation of the fiber filler material, the foam wedge, and the unitary interior and exterior covering fabrics.

FIG. 8 is a cutaway view of the medical boot as seen from the perspective of cutaway line A-A depicted in FIG. 3. Most prominent in this view are the left sidewall 9, which is shown to be filled with a suitable fiber 8 material, and the right sidewall 10, also filled with fiber 8. The fiber 8 is contained in the sidewalls 9, 10, by the outer fabric 25 and the inner fabric 26. The outer fabric 25 extends around to enclose the boot outer bottom 33 also filled with fiber 8. As can be seen in FIG. 8, the cross-section of the foam wedge 1 illustrates how the fiber 8 material lays upon the top surface edge of the foam wedge 1, thereby providing a patient with the benefit of cushioning from both the fiber 8 and the resilient foam wedge 1. The inner fabric 26 covers the inner surfaces of the left and right sidewalls 9, 10, and further serves to contain the fiber 8 that is placed on the top surface of the foam wedge 1 at the inner base 5 of the medical boot. The inner fabric 26 is also shown to cover the left foot portion 6 of the boot and the right foot portion 7 of the boot. Also discernable in FIG. 8 are the left sewn hook piece 21 and the right sewn hook piece 22. Both sewn hook pieces 21, 22 are sewn into the outer fabric 25 and each forms the hook component of a hook-and-loop fastening system. So as to engage the loop component of the left Y-strap loop fastener 17 and the right Y-strap loop fastener 14, respectively.

Figure 9:
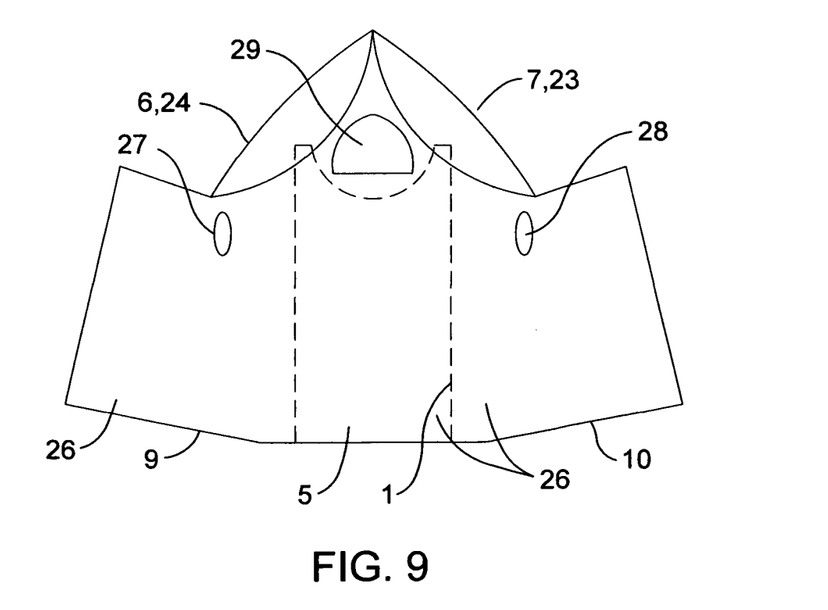
FIG. 9 presents the form of the one-piece exterior material prior to stitching onto the completed device.

FIG. 9 is a total laid-out view of the unitary interior body form, or material pattern, of the medical boot. A dashed outline depicts the relative location of the foam wedge 1 as it would be placed under the inner fabric 26 just prior to stitching the medical boot closed to form the base 5 of the boot. Also shown in FIG. 9 are the boot heel opening 29, the left sidewall 9, the right sidewall 10, the left tube hole 27, and the right tube hole 28. The inner fabric 26 of the boot utilizes a material that has two beneficial features. The first quality is that the inner fabric 26 is antibacterial, meaning it will not allow bacteria to grow and further, creates an environment hostile to the spread of any strain of bacteria inadvertently introduced into the medical boot. The second feature is that the inner fabric 26 absorbs moisture or other body fluids that may be produced by the patient. The unitary exterior body form, which may comprising a "rip-stop" type exterior fabric, is an exact superimposed image of the unitary interior body form.

The left and right tube holes 27, 28 may often be required for the insertion of medical tubing. The primary medical tubing that would typically be used in conjunction with a pressure relief boot would be a sequential compression pump. Many patients that would require a boot as disclosed herein would probably also need the use of medical tubing. Thus, the left and right tube holes 27, 28 allow for the use of said tubing while still taking advantage of the pressure relief characteristics of the boot.

Figure 10:
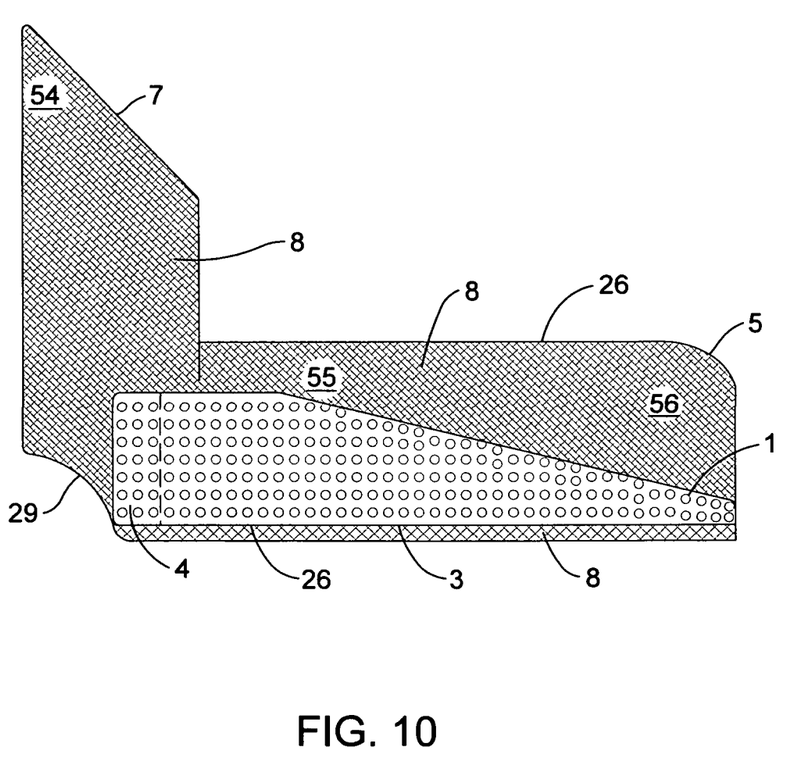
FIG. 10 is stylized to show the relationship between the foam wedge material and the fiber material, which are both incorporated into the device.

FIG. 10 is a stylized rendition of the relationship of the various materials used in the construction of the medical boot. As seen from left to right, the left and/or right foot portions of the boot 6, 7 are filled to capacity in what is essentially the toe fiber fill area 54, with a suitable fiber 8 material. A profile view of the foam wedge 1 is shown as the foam wedge bottom 3 rests atop a thin layer of inner fabric 26 and fiber 8. In the fabrication of the medical boot, the foam/fiber combination provides a unique blending of materials for patient comfort. On the upper surface of the foam wedge 1, fiber is placed strategically at the locations of the Achilles tendon fiber fill area 55, and the patient's calf fiber fill area 56 and also packed into the spaces between these three locations. The purpose of the fiber 8 is to cushion the bony areas of the patient's lower leg 31 and prevent pressure sores that can be caused by the use of foam support only.

While preferred embodiments of the present inventive concept have been shown and disclosed herein, it will be obvious to those persons skilled in the art that such embodiments are presented by way of example only, and not as a limitation to the scope of the inventive concept. Numerous variations, changes, and substitutions may occur or be suggested to those skilled in the art without departing from the intent, scope, and totality of this inventive concept. Such variations, changes, and substitutions may involve other features which are already known per se and which may be used instead of, in combination with, or in addition to features already disclosed herein. Accordingly, it is intended that this inventive concept be inclusive of such variations, changes, and substitutions, and by no means limited by the scope of the claims presented herein.

What is claimed is:

1. A heel and lower leg-supporting medical foot boot for bed patients, comprising
    a unitary interior body form and material pattern, having an inner base section, left and right foot sections, left and right sidewall sections, and a heel opening;
    a unitary exterior body form having, an outer bottom, left and right foot sections, left and right sidewall sections, and a heel opening, said unitary exterior body form corn the same material pattern being of a same contour and dimensions as the interior body form;
    fiber filling;
    an angled foam wedge having a circular cutout;
    left and right Y-straps;
    left and right Y-strap loop fasteners;
    left and right sewn hook pieces;
    a horizontal hook strap;
    upper and lower loop straps;
    a T-stabilizer;
    a stabilizer pocket integral to the outer bottom of said unitary exterior body form, said stabilizer pocket of inner dimensions corresponding to the dimensions of said T-stabilizer; and
    left and right bottom straps; wherein
said interior and exterior body forms are joined by superimposing each on the other and stitching their corresponding perimeters together subsequent to a) inserting fiber filing into the combined inner base and outer bottom sections, foot sections, and sidewall sections and b) placing said angled foam wedge between layers of fiber filling within the combined inner base and outer bottom sections of the respective unitary body forms.

2. The heel and lower leg-supporting medical foot boot for bed patients as in claim 1, further comprising a color-coding system whereby a) said upper and lower loop straps and said horizontal strap all comprise a first color and b) said left and right Y-strap loop fasteners and said left and right sewn pieces all comprise a second color.

3. The heel and lower leg-supporting medical foot boot for bed patients as in claim 1, wherein said unitary exterior body form comprises a "rip-stop" type fabric, and said unitary interior body form comprises a brushed micro-suede type fabric that is anti-bacterial and water-repellant.

4. A heel and lower leg-supporting medical foot boot for bed patients, comprising
    a unitary interior body form and material pattern having an inner base section, left and right foot sections, left and right sidewall sections, left and right tube holes, and a heel opening;
    a unitary exterior body form having an outer bottom, left and right foot sections, left and right sidewall sections, left and right tube holes, and a heel opening said unitary exterior body form comprising the same material pattern being of a same contour and dimensions as the interior body form;
    fiber filling,
    an angled foam wedge having a circular cutout;
    left and right Y-straps;
    left and right Y-strap loop fasteners;

left and right sewn hook pieces, attached to said left and right sidewalls formed by said exterior body form;
a horizontal hook strap attached to the left exterior sidewall;
upper and lower loop straps attached to the right top seam of said right sidewall;
a stabilizer pocket attached to the outer bottom of said unitary exterior body form;
a T-stabilizer having a stem, a left slot, and a right slot, wherein the stem of said T-stabilizer comprises dimensions allowing insertion of said T-stabilizer into said stabilizer pocket;
left and right bottom straps attached to the outer bottom of said unitary exterior body form; and
a "Toes" tag sewn onto the boot front seam, wherein
said interior and exterior body forms are joined by superimposing each on the other and stitching their corresponding perimeters together subsequent to a) inserting fiber filing into the combined inner base and outer bottom sections, foot sections, and sidewall sections and b) placing said angled foam wedge between layers of fiber filling placed within the combined inner base and outer bottom sections of the respective unitary body forms.

5. The heel and lower leg-supporting medical foot boot for bed patients as in claim 4, further comprising a color-coding system whereby a) said upper and lower loop straps and said horizontal strap all comprise a first color and b) said left and right Y-strap loop fasteners and said left and right sewn pieces all comprise a second color.

6. The heel and lower leg-supporting medical foot boot for bed patients as in claim 4, wherein said unitary exterior body form comprises a "rip-stop" type fabric, and said unitary interior body form comprises a brushed micro-suede type fabric that is anti-bacterial and water-repellant.

* * * * *